US011692197B2

United States Patent
Issa et al.

(10) Patent No.: US 11,692,197 B2
(45) Date of Patent: Jul. 4, 2023

(54) DELIVERY OF BIOLOGICAL MOLECULES TO PLANT CELLS

(71) Applicant: INARI AGRICULTURE TECHNOLOGY, INC., Cambridge, MA (US)

(72) Inventors: John Paul Issa, Medford, MA (US); Grethel Yanet Busot, Belmont, MA (US)

(73) Assignee: INARI AGRICULTURE TECHNOLOGY, INC., Cambridge, MA (US)

(*) Notice: Subject to any disclaimer, the term of this patent is extended or adjusted under 35 U.S.C. 154(b) by 0 days.

(21) Appl. No.: 16/855,753

(22) Filed: Apr. 22, 2020

(65) Prior Publication Data

US 2020/0354732 A1  Nov. 12, 2020

Related U.S. Application Data

(60) Provisional application No. 62/843,941, filed on May 6, 2019.

(51) Int. Cl.
*C12N 15/82* (2006.01)
*C12N 15/10* (2006.01)

(52) U.S. Cl.
CPC ..... *C12N 15/8201* (2013.01); *C12N 15/1013* (2013.01); *C12N 2310/20* (2017.05)

(58) Field of Classification Search
None
See application file for complete search history.

(56) References Cited

U.S. PATENT DOCUMENTS

| | | |
|---|---|---|
| 5,753,477 A | 5/1998 | Chan |
| 8,232,192 B2 | 7/2012 | Lin et al. |
| 8,722,410 B2 | 5/2014 | Samuel et al. |
| 9,187,755 B2 | 11/2015 | Samuel et al. |
| 9,339,539 B2 | 5/2016 | Xing et al. |
| 9,707,294 B2 | 7/2017 | Xing et al. |
| 9,719,108 B2 | 8/2017 | Samuel et al. |
| 2010/0298816 A1 | 11/2010 | Dobson |
| 2015/0059010 A1 | 2/2015 | Cigan et al. |
| 2015/0082478 A1 | 3/2015 | Cigan et al. |
| 2015/0344912 A1 | 12/2015 | Kim et al. |
| 2016/0138008 A1 | 5/2016 | Doudna et al. |

FOREIGN PATENT DOCUMENTS

| | | |
|---|---|---|
| CN | 102925488 B | 3/2015 |
| WO | 2015131101 A1 | 9/2015 |
| WO | 2016007347 A1 | 1/2016 |
| WO | 2016/166340 A1 | 10/2016 |

OTHER PUBLICATIONS

Zhao, Pollen magnetofection for genetic modification with magnetic nanoparticles as gene carriers, Nature Plants, vol. 3, Dec. 2017, pp. 956-964 (Year: 2017).*
Vainauska, A Novel Approach for Nucleic Acid Delivery Into Cancer Cells, Medicina (Kaunas), 2012, pp. 324-329 (Year: 2012).*
Hryhorowicz, Improved Delivery of CRISPR/Cas9 System Using Magnetic Nanoparticles into Porcine Fibroblast, Molecular Biotechnology, Dec. 17, 2018 (Year: 2018).*
Meyer, A genomic DNA segment from Petunia hybrida leads to increased transformation frequencies and simple integration patterns, Proceedings of the National Academy of Sciences, Nov. 1988 (Year: 1998).*
Wang, A Magnetic Nanoparticle-Based Multiple-gene Delivery System for Transfection of Porcine Kidney Cells, PLOS one, published Jul. 21, 2014 (Year: 2014).*
Li, Optimization of Agrobacterium-mediated transformation in Soybean, Frontiers in Plant Science, Feb. 2017 (Year: 2017).*
Que, Repurposing macromolecule delivery tools for plant genetic modification in the Era of Precision Genome Engineering, Transgenic Plants: Method and Protocols, Methods in Molecular Biology, Published online Nov. 2018 (Year: 2018).*
McBain, S. C., et al. "Magnetic nanoparticles as gene delivery agents: enhanced transfection in the presence of oscillating magnet arrays." Nanotechnology 19.40 (2008): 405102. (Year: 2008).*
Kamau, Sarah W., et al. "Enhancement of the efficiency of non-viral gene delivery by application of pulsed magnetic field." Nucleic Acids Research 34.5 (2006): e40-e40. (Year: 2006).*
Harkess, Twitter Blog, 12 pages, retrieved from https://twitter.com/aeharkess?lang=en on May 7, 2019.
Harkess, Twitter Blog, retreived from <https://twitter.comaeharkessstatus1040440428288503808 on Apr. 30, 2020, 1 page.
Harkess, Twitter Blog, retrieved from <https://twitter.comaeharkessstatus1040440428288503808> on Apr. 30, 2020, 7 pages.
Magnetofection For Primary and Hard-to-Transfect Cells, OZBiosciences, 2018, 8 pages.
Magnetofection The New Gene Transfection Technology, Chemicell, 41 pages.
Magnetofection™ PolyMag and PolyMag Neo Instruction Manual, OZ Biosciences, 10 pages.
Magro et al., "Cobalently Bound DNA on Naked Iron Oxide Nanoparticles: Intelligent Colloidal Nano-vector for Cell Transfection", BBA General Subjects, 2017, 9 pages.
PubPeer blog post about, Zhao et al., "Pollen Magnetofection for Genetic Modification with Magnetic Nanoparticles as Gene Carriers", Nature Plants, 2019, 13 pages.

(Continued)

*Primary Examiner* — Weihua Fan
*Assistant Examiner* — Brian James Sullivan
(74) *Attorney, Agent, or Firm* — McKee, Voorhees & Sease, PLC

(57) ABSTRACT

Methods and systems for delivering biological materials such as nucleic acids and/or proteins to the interior of a plant cell are provided. Such methods and systems include those where biological material is non-covalently complexed with a magnetic particle and accelerated multiple times toward a plant cell.

22 Claims, No Drawings

(56) References Cited

OTHER PUBLICATIONS

Theumer et al., "Superparamagnetic Iron Oxide Nanoparticles Exert Different Cytotoxic Effects on Cells Grown in Monolayer Cell Culture Versus as Multicellular Spheroids", Journal of Magnetism and Magnetic Materials, 2015, pp. 27-33, vol. 380.
Wang et al., "Interaction of Gold Nanoparticles with Proteins and Cells", Sci, Technol. Adv. Mater., 2015, 15, pages, vol. 16.
Zhao et al., "Pollen Magnetofection for Genetic Modification with Magnetic Nanoparticles as Gene Carriers", Nature Plants, 2017, pp. 956-964, vol. 3.
Zhao et al., "Pollen Magnetofection for Genetic Modification with Magnetic Nanoparticles as Gene Carriers", Nature Plants, 2017, 53 pages, Supplemental.
Negrutiu et al., "Hybrid genes in the analysis of transformation conditions : I. Setting up a simple method for direct gene transfer in plant protoplasts", Abstract, Plant Mol Biol., vol. 8, No. 5, doi: 10.1007/BF00015814, pp. 363-373, 1987.
Shillito et al., "High Efficiency Direct Gene Transfer to Plants", Abstract, Bio/Technology, vol. 3, pp. 1099-1103, 1985.
Department of Genetics and Genome Biology, "The Pollen Wall", University of Leicester, 1 page, 2021; downloaded on Oct. 11, 2021 from https://www2.le.ac.uk/departments/genetics/people/twell/lab/pollenis/wall.
Vejlupkova et al., "No evidence for transient transformation via pollen magnetofection in several monocot species", Nature Plants, vol. 6, pp. 1-7, 2020.

\* cited by examiner

DELIVERY OF BIOLOGICAL MOLECULES TO PLANT CELLS

CROSS-REFERENCE TO RELATED APPLICATIONS

This application claims benefit of priority to U.S. Provisional Patent Application No. 62/843,941 filed May 6, 2019, which is incorporated herein by reference in its entirety.

FIELD

Aspects of this disclosure relate to biotechnology, in particular compositions and methods for plant transformation.

BACKGROUND

Plant transformation methods have been used to produce transgenic plants, i.e., plants modified to contain a transgene, for several decades. More recently, genome editing methods (e.g., using nucleases such as zinc-finger nucleases (ZFNs), transcription activator-like effector nucleases (TAL-effector nucleases or TALENs), and RNA-guided nucleases such as CRISPR Cas nucleases) not requiring introduction of a transgene into a plant genome have been developed. Genome editing agents can be provided to a plant cell by transformation with polynucleotides (e.g., polynucleotides encoding sequence-specific nucleases) or by direct delivery into the plant cell of the genome editing agent(s) (e.g., a ribonucleoprotein including an RNA-guided sequence-specific nuclease and a guide RNA).

Protocols for delivery of biological molecules to plant cells that have been used with varying degrees of success include microinjection, electroporation, and biolistics; these have various disadvantages in that these techniques can be cumbersome (e.g., microinjection), work best in protoplasts (e.g., electroporation), or generally require tissue culture through callus (e.g., biolistics). Some plant transformation approaches utilize the natural ability of certain viruses (or viral-derived sequences such as replicons, see, e.g., Baltses et al. (2014), *Plant Cell,* 26:151-163) or bacteria to transfer genetic material into a plant cell. However, both virally mediated and bacterially mediated transformation techniques may face regulatory hurdles. *Agrobacterium tumefaciens*-mediated transformation, the most commonly used bacterially mediated technique (see, e.g., Bourras et al. (2015) *Phytopathol.,* 105:1288-1301), is limited to the transfer of DNA, results in the integration of bacterially derived "T-DNA" sequences in the plant cell's genome, generally requires tissue culture through callus, and has been useful only with certain plant species or even varieties or germplasm within a given species. Furthermore, all of these existing delivery or transformation methods typically require subjecting the transformed plant material or explants to tissue culture through a dedifferentiated callus phase, and often involve selection with an antibiotic or herbicide (thus requiring the corresponding antibiotic or herbicide resistance transgene to be incorporated into the transformed plant). See, e.g., Gordon-Kamm et al. (1990) *Plant Cell,* 2:603-618. Transformed plants that contain an introduced transgene for such selection are generally subject to stringent regulatory requirements. Removal of such an introduced transgene generally requires at least one crossing or backcrossing step, which itself can introduce unwanted genomic changes in the resulting progeny plants.

Plant tissue culture as used in the production of transformed plants results in significant changes (typically a decrease) in genome methylation status and heritable epigenome changes in the resulting transformed plants; this may lead to unintended phenotypic changes or unwanted somaclonal variation in the resulting transformed plants. See, e.g., Stroud et al. (2013) eLife 2:e00354; DOI:10.7554/eLife.00354; Stelpflug et al. (2014) *Genetics,* 198:209-218. Furthermore, crop plants such as soybean are often commercially provided as "elite germplasm", or inbred lines that have been selectively bred and optimized for a given growing condition or region; not all germplasm or inbred lines are equally amenable to transformation using tissue culture.

For at least the above reasons, methods of delivering biological molecules, such as transformation agents or genome editing agents, that can be applied to various plant species, preferably without limitation to specific genotypes, and that do not require use of selection or tissue culture through a callus stage, are advantageous.

SUMMARY

Disclosed herein are compositions and methods useful for delivering biological molecules such as genome editing agents to a plant cell, and that do not require use of a selectable marker or of tissue culture through a callus stage.

In one aspect, this disclosure describes a method of delivering an exogenous biological material to the interior of a plant cell, wherein the biological material is non-covalently complexed with a magnetic particle, such as a magnetic nanoparticle; and wherein the magnetic particle is accelerated toward a plant cell multiple times; whereby the biological material is delivered to the interior of the plant cell. In embodiments, the method employs ferromagnetic or superparamagnetic nanoparticles that are accelerated toward a plant cell multiple times (e.g., at least 2, 3, 4, 5, 6, 7, or 8, or even more accelerations), for example by repeatedly placing the plant cell in proximity to a permanent magnet or other non-oscillating (static) magnetic field in proximity and then separating the plant cell and the magnetic field. The method is useful for delivering various biological materials and chemically modified biological materials to the interior of a plant cell. Embodiments include delivery of polynucleotides, polypeptides, or combinations of both polynucleotides and polypeptides, to the interior of a plant cell. Particular embodiments include delivery of sequence-specific genome editing agents, such as sequence-specific nucleases (or polynucleotides encoding such nucleases) or ribonucleoproteins including a sequence-specific nuclease, to the interior of a plant cell. In some embodiments the method is useful for delivering polynucleotides encoding sequence-specific genome editing agents, such as DNA encoding base editors or DNA encoding CRISPR nucleases and associated guide RNAs and donor polynucleotides. In embodiments, the plant cell has intact cell walls, which have not been damaged by chemical, enzymatic, or physical means. In embodiments, the plant cell is located in a plant tissue, such as in a pollen grain, an ovule, an embryo, or a seed. In embodiments, the plant cell is haploid. In embodiments, the plant cell is a cell of a haploid inducer plant. In specific embodiments, a sequence-specific genome editing agent, such as a sequence-specific nuclease (or a polynucleotide encoding such a nuclease), is delivered to a plant cell located in a pollen grain, and at least one non-random genomic modification is effected by the genome editing agent in the plant cell; in some embodiments, the method further includes the steps of germinating the pollen grain to form a pollen tube, and contacting the resulting pollen tube with female reproductive tissue or cells of a maternal plant, thereby resulting in fertilization of an egg of the maternal plant. The method of use particularly in effecting non-random genomic modifications of dicot plants, such as, but not limited to, leguminous plants (e.g., soybean) or solanaceous plants (e.g., tomato, pepper), including dicot plants of elite germplasm or of inbred lines. Related aspects of this disclosure include the plant cell into which the exogenous biological material has been delivered (e.g., a plant cell in which a genomic modification has been effected by an exogenous sequence-specific genome editing agent that was delivered using the disclosed method), as well as progeny plant cells, tissue, plants, or seeds grown from or regenerated from the plant cell.

In one aspect, this disclosure describes a method of providing a genome editing agent to a plant cell, including multiple applications of a magnetic field to a composition including: (a) a plant tissue containing a plant cell; and (b) approximately spherical magnetic nanoparticles of about 150 to about 300 nanometers in diameter that are non-covalently complexed with a genome editing agent; whereby the genome editing agent is delivered to the interior of the plant cell. In embodiments, the method results in a non-random genomic modification of the plant cell. In embodiments, the genome editing agent is a polynucleotide, a polypeptide, or a combination of both a polypeptide and a polynucleotide (e.g., a ribonucleoprotein including an RNA-guided sequence-specific nuclease and a guide RNA). In embodiments, the plant tissue is male or female reproductive tissue containing haploid cells. In embodiments, the plant cell is a cell of a haploid inducer plant. In one embodiment, the plant tissue is a pollen grain, e.g., a dicot or a monocot pollen grain. In one embodiment, the plant tissue is a pollen grain collected pre-anthesis. In embodiments, the composition further includes exogenously provided DNA, such as exogenously provided non-specific ssDNA or dsDNA or a mixture of ssDNA and dsDNA. Related aspects of this disclosure include the plant cell (or the plant tissue containing the plant cell) into which the genome editing agent has been delivered (e.g., a plant cell in which a genomic modification has been effected by an exogenous sequence-specific genome editing agent that was delivered using the disclosed method), as well as progeny plant cells, tissue, plants, or seeds grown from or regenerated from the plant cell.

Additional aspects of the disclosure provide a plant modification system including: (a) a sequence-specific nuclease (e.g., a Cas nuclease or Cas nuclease ribonucleoprotein) non-covalently complexed with a magnetic nanoparticle; (b) a pollen grain; (c) liquid medium containing exogenous non-specific DNA (e.g., salmon sperm DNA). In embodiments, the magnetic nanoparticle is spherical and is about 150 to about 300 nanometers in diameter. In embodiments, the pollen grain is a pre-anthesis-stage dicot pollen grain. In embodiments, the liquid medium contains exogenous non-specific DNA of an average size of ≤2,000 bp at a concentration of between 0.05-1 milligrams per microliter; in specific embodiments the liquid medium contains exogenous non-specific DNA of an average size of ≤2,000 bp at a concentration of between 0.1-0.5 milligrams per microliter. In embodiments, the plant modification system further includes at least one of the following: one or more donor polynucleotides, one or more cell-penetrating peptides, and one or more nuclear localization signals. In embodiments, the plant modification system further includes a magnetic field, such as a non-oscillating magnetic field. Related aspects of this disclosure include the plant cell (or the plant tissue containing the plant cell) in which a genomic modification has been effected by use of the plant modification system, as well as progeny plant cells, tissue, plants, or seeds grown from or regenerated from the plant cell.

Embodiments of the method further include the steps of regenerating fertile T0 plants and obtaining progeny T1 seed and T1 plants. Where the method involves delivery of sequence-specific genome editing molecules, the method is useful for producing T0 and progeny plants of subsequent generations that have a genome that is essentially (>99%) identical to that of the original, unmodified genome, except for the sequence-specific genome edits effected by the method. Also provided by the disclosure are transformed T0 plants and progeny plants of the T1 and further generations, including hybrid progeny plants. Because the method does not require tissue culture through a callus phase, the T0 plants (and progeny T1 seeds or T1 plants) do not exhibit the degree of epigenetic changes (such as hypomethylation) that is observed in genome-edited plants that are produced using tissue culture procedures that involve a callus phase. Depending on the genome editing agent(s) used, the at least one genetic modification in the genome-edited germline cells and the resulting T0 plants can be characterized as single or multiplexed genomic edits. For example, in embodiments of the method, the biological molecule or genome editing agent includes or encodes a sequence-specific nuclease such as a CRISPR Cas nuclease, and the T0 plant contains a genome that has been edited by the sequence-specific nuclease; various examples of such "genomic edits" include deletion of one or more nucleotides, insertion of one or more nucleotides, insertion of a nucleotide sequence encoded by a donor polynucleotide, allele substitution or replacement, and combinations of such genomic changes. Also encompassed by the disclosure are raw plant materials, processed plant products, and commodity plant products obtained from a T1 plant, T1 plant cell, T1 plant tissue, or T1 seed (or from progeny plants or seeds thereof).

DETAILED DESCRIPTION

Where a term is provided in the singular, the inventors also contemplate aspects described by the plural of that term.

"CRISPR (Clustered Regularly Interspaced Short Palindromic Repeats)/Cas (CRISPR-associated) systems," or CRISPR systems, are adaptive defense systems originally discovered in bacteria and archaea. CRISPR systems use RNA-guided nucleases termed CRISPR-associated or "Cas" endonucleases (e.g., Cas9 or Cas12a ("Cpf1")) to cleave foreign DNA. In atypical CRISPR/Cas system, a Cas endonuclease is directed to a target nucleotide sequence (e.g., a site in the genome that is to be sequence-edited) by sequence-specific, non-coding "guide RNAs" that target single- or double-stranded DNA sequences.

CRISPR-type genome editing has value in various aspects of agriculture research and development. CRISPR elements, e.g., CRISPR endonucleases and CRISPR single-guide RNAs, are useful in effecting genome editing without remnants of the CRISPR elements or selective genetic markers occurring in progeny. Alternatively, genome-inserted CRISPR elements are useful in plant lines adapted for multiplex genetic screening and breeding. For instance, a plant species can be created to express one or more of a CRISPR endonuclease such as a Cas12a-type endonuclease or combinations with unique PAM recognition sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for trait introgression. Multiple endonucleases can be provided in expression cassettes with the appropriate promoters to allow multiple genome editing in a spatially or temporally separated fashion in either in chromosome DNA or episome DNA.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cas12a (Cpf1) endonuclease and corresponding guide RNAs and PAM sites are disclosed in U.S. Pat. No. 9,790,490 and U.S. patent application Ser. No. 15/566,528 (national phase of PCT Application PCT/EP2016/058442, published as WO 2016/166340). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety.

At least one double-stranded break (DSB) can be effected at a precisely determined site in the plant genome, for example by means of an RNA-guided nuclease and guide RNAs, and a nucleotide sequence encoded by a donor polynucleotide can then be heterologously integrated at the site of the DSB (or between two DSBs). In embodiments, the donor polynucleotide includes single-stranded DNA, optionally including chemical modifications. In other embodiments, the donor polynucleotide includes double-stranded DNA, optionally including chemical modifications. In some embodiment the donor polynucleotide includes both DNA and RNA, for example as a duplex formed by a DNA strand and an RNA strand. In embodiments, the donor polynucleotide is designed to include a template for genome editing via homology-dependent repair (HDR); the template generally includes a "core sequence" that is to replace a sequence of the genome of about the same size, as well as "homology arms" that flank the core sequence on either side and have a sequence complementary to the genomic regions flanking the genomic sequence to be replaced or edited. In other embodiments, the donor polynucleotide does not include homology arms or does not include a core sequence and homology arms, for example in embodiments where the donor polynucleotide is used to make a deletion, or is used to integrate a polynucleotide sequence by a non-homologous end-joining (NHEJ) mechanism.

In general, a donor polynucleotide including a template encoding a nucleotide change over a region of less than about 50 nucleotides is conveniently provided in the form of single-stranded DNA; larger donor templates (e.g., more than 100 nucleotides) are often conveniently provided as double-stranded DNAs. Thus in some embodiments, the donor polynucleotide is about 25 nucleotides, 50 nucleotides, 60 nucleotides, 70 nucleotides 80 nucleotides, 90 nucleotides, 100 nucleotides, 200 nucleotides, 300 nucleotides, 400 nucleotides, 500 nucleotides, 600 nucleotides, 700 nucleotides, 800 nucleotides, 900 nucleotides, 1000 nucleotides, 1200 nucleotides, 1500 nucleotides, 1800 nucleotides, 2000 nucleotides, 2500 nucleotides, 3000 nucleotides, 5000 nucleotides, 10,000 nucleotides, or more (such as about 25-200 nucleotides, 50-300 nucleotides, 100-500 nucleotides, 200-800 nucleotides, 700-2000 nucleotides, 1000-2500 nucleotides, 2000-5000 nucleotides, 4000-8000 nucleotides, or 6000-10,000 nucleotides).

The term "heterologous" describes a nucleic acid sequence that is positioned out of its naturally occurring or native context; the term also describes two adjacent nucleic acid sequences that do not naturally occur together (but are not necessarily from different species). The term "heterologous" is also used to refer to a given sequence in relationship to another—e.g., the sequence of a donor polynucleotide molecule is heterologous to the sequence of the genomic locus wherein the polynucleotide is integrated. For example, a ubiquitin promoter sequence can be used to drive expression of a gene (for example, luciferase) other than the ubiquitin gene natively driven by the promoter; in this case the ubiquitin promoter is "heterologous" to the luciferase gene (and vice versa), and the ubiquitin promoter and luciferase gene are in a heterologous arrangement relative to each other. By "integration of heterologous sequence" is also meant integration or insertion of one or more nucleotides, resulting in a sequence (including the inserted nucleotide(s) as well as at least some adjacent nucleotides of the genomic sequence flanking the site of insertion at the DSB) that is itself heterologous, i.e., would not otherwise or does not normally occur at the site of insertion.

Whether an explant, plantlet, or T0 plant has been transformed can be determined by observing phenotype or by genotyping or by both. For the purposes of this disclosure and when referring to the claimed methods, systems, compositions, and transformed plants and seeds, "transformation efficiency" is conveniently expressed as a percentage, and is measured by dividing the total number of genotyped "positive" (that is, stably transformed) T0 plants by the total number of explants that were subjected to the transformation method, the result expressed as a percentage. Genotyping is carried out by any convenient technique, such as by PCR amplification to determine the presence of a nucleic acid sequence expected to be present in a successfully transformed plant.

Method of Delivering an Exogenous Biological Material to the Interior of a Plant Cell This disclosure provides a method of delivering a biological material to the interior of a plant cell, the method including accelerating a biological material that is non-covalently complexed with a magnetic particle multiple times toward a plant cell, whereby the biological material is delivered to the interior of the plant cell.

In embodiments, the biological material is a naturally occurring biological material (e.g., a polypeptide isolated from a natural source), or is a recombinantly produced biological material (e.g., a ribonucleoprotein including a recombinantly produced Cas nuclease and a recombinantly produced guide RNA), or is a chemically modified biological material (e.g., a sequence-specific nuclease labelled with a fluorophore or other detectable label). Embodiments of the method are useful for delivering polynucleotides, polypeptides, or combinations of both polynucleotides and polypeptides to the interior or a plant cell. In embodiments, the biological material is a macromolecule, such as a protein, a complex of proteins covalently or non-covalently associated with each other, or a ribonucleoprotein. Generally, the biological material does not include an intact virus or viroid. Embodiments of the method that are particularly useful for effecting non-random genomic modification of plant cells include delivery of sequence-specific genome editing agents, such as sequence-specific nucleases (e.g., Cas nucleases) or polynucleotides encoding such nucleases, or ribonucleoproteins including a sequence-specific nuclease, to the interior of a plant cell. See also the paragraphs captioned "Genome Editing Agents" in the "Related Disclosure" section of this disclosure. In some embodiments the method is useful for delivering polynucleotides encoding sequence-specific genome editing agents, such as DNA encoding base editors or DNA encoding Cas nucleases and associated guide RNAs and donor polynucleotides. In embodiments, the biological material includes a polynucleotide (e.g., DNA, RNA, or a combination of DNA and RNA), which can be isolated from a natural source, or synthetically produced; such polynucleotides can be chemically or biochemically modified, e.g., to improve stability or solubility. In embodiments, the biological material includes a polypeptide (such as a sequence-specific nuclease) having a sequence that is codon-optimized for the plant (dicot or monocot), as is best suited. In embodiments, the biological material consists essentially of one or more polynucleotides but includes no protein. In other embodiment, the biological material includes a polypeptide (e.g., a sequence-specific nuclease, a reporter protein such as a fluorescent protein) or a ribonucleoprotein (e.g., a Cas nuclease and its associated guide RNA and optional donor polynucleotide); such polypeptides can be chemically or biochemically modified, e.g., to incorporate a fluorescent label, a nuclear localization signal (NLS), or a cell-penetrating peptide (CPP). In embodiments, the biological material includes a sequence-specific genome editing agent, such as at least one genome editing agent selected from the group consisting of a sequence-specific nuclease, a ribonucleoprotein including a Cas nuclease and its associated guide RNA, a guide RNA, and a donor polynucleotide; or one or more polynucleotides encoding such. In embodiments, the biological material includes a sequence-specific genome editing agent, such as a deactivated sequence-specific nuclease (e.g., a "dead" Cas nuclease), which can be complexed with other polypeptides (e.g., polypeptides including a functional domain) or with polynucleotides or with both. In embodiments, the biological material is small in size (e.g., less than 10 nanometers in diameter for a globular protein), relative to viruses.

The biological material is non-covalently complexed with a magnetic particle, such as a magnetic nanoparticle. In embodiments, the method employs ferromagnetic or superparamagnetic nanoparticles. In embodiments, the magnetic particle is approximately spherical, i.e., the dimensions are approximately equal in all directions, unlike a particle shaped like a rod, tube, or needle. In embodiments, the magnetic particle is an approximately spherical magnetic nanoparticle of about 150 to about 300 nanometers in diameter. In embodiments, the magnetic nanoparticle is surface-modified, e.g., to modify the average charge or polarity on the nanoparticle's surface. In embodiments, the magnetic particle is a nanoparticle comprising iron oxides (e.g., PolyMag or PolyMag Neo reagents, available from OZ Biosciences, Inc., San Diego, Calif.). In embodiments, the magnetic particle is a nanoparticle comprising iron oxides mixed with or coated with a synthetic polymer, such as polyethyleneimine. In embodiments, the magnetic particle is a nanoparticle comprising a gold-coated iron oxide core or "magnetic core gold nanoshell" (e.g., "Magnetic 150 nm Gold Nanoshells" or "Magnetic 280 nm Gold Nanoshells", available from nanoComposix, Inc., San Diego, Calif.), which are optionally surface-modified (e.g., with carboxyl groups).

In embodiments, the plant cell is a cell of a dicot plant. In other embodiments, the plant cell is a cell of a monocot plant. In embodiments, the plant cell is located in a plant tissue, such as in at least one plant tissue selected from the group consisting of an intact nodal bud, a shoot apex or shoot apical meristem, a root apex or root apical meristem, lateral meristem, intercalary meristem, a seedling (e.g., a germinating seed or small seedling or a larger seedling with one or more true leaves), leaf tissue, a whole seed (e.g., an intact seed, or a seed with part or all of its seed coat removed or treated to make permeable), a halved seed or other seed fragment, an embryo (e.g., a mature dissected zygotic embryo, a developing embryo, a dry or rehydrated or freshly excised embryo) or embryonic tissue, an anther, a stigma, a style, an ovule, an ovary, and callus. In embodiments, the plant cell is in pollen (i.e., in a pollen grain). In embodiments, the plant cell is in a pre-hydrated pollen grain. In embodiments, the plant cell is located in a pre-anthesis pollen grain. In embodiments, the plant cell is located in a pre-anthesis-stage dicot pollen grain. In a specific embodiment, the plant cell is from a soybean plant and is located in a pre-anthesis-stage soybean pollen grain. In embodiments, the plant cell is haploid. In embodiments, the plant cell is a cell of a haploid inducer plant, such as a cell in a pollen grain of a haploid inducer plant. The method can also be used with individual plant cells (i.e., not in a tissue), such as plant cells in suspension (e.g., cultured plant cells in liquid medium) or fixed onto a solid surface or matrix. In embodiments, the plant cell, or a tissue containing the plant cell, is provided in a composition including exogenous non-specific DNA (e.g., non-specific double-stranded DNA, non-specific single-stranded DNA, commercially available sheared salmon sperm DNA). In an embodiment, the plant cell is provided in a composition including exogenous non-specific DNA at a concentration of between 0.05-1 milligrams per microliter; in a specific embodiment, the plant cell is provided in a composition including exogenous non-specific DNA at a concentration of between 0.1-0.5 milligrams per microliter. In an embodiment, the plant cell is in a pollen grain provided in a composition including exogenous non-specific DNA at a concentration of between 0.05-1 milligrams per microliter. In an embodiment, the plant cell is in a dicot pollen grain provided in a composition including exogenous non-specific DNA of an average size of ≤2,000 bp at a concentration of between 0.05-1 milligrams per microliter. In a specific embodiment, the method includes accelerating, by means of a non-oscillating magnetic field, a biological material that includes a ribonucleoprotein (RNP) including a Cas nuclease and a guide RNA and that is non-covalently complexed with an approximately spherical magnetic nanoparticle of about 150 to about 300 nanometers in diameter multiple times toward a plant cell, whereby the biological material is delivered to the interior of the plant cell. In a specific embodiment, the method includes accelerating, by means of a permanent magnet, a biological material that includes a ribonucleoprotein (RNP) including a Cas nuclease and a guide RNA and that is non-covalently complexed with an approximately spherical magnetic nanoparticle of about 150 to about 300 nanometers in diameter multiple (e.g., at least 2, 3, 4, 5, 6, 7, 8, 9, or 10) times toward a plant cell in a dicot pollen grain provided in a composition including exogenous non-specific DNA of an average size of ≤2,000 bp (e.g., UltraPure™ Salmon Sperm DNA Solution (Invitrogen™), catalogue number 15632011, Thermo Fisher Scientific, Waltham, Mass.) at a concentration of between 0.1-0.5 milligrams per microliter, whereby the biological material is delivered to the interior of the plant cell.

Generally, the plant cell is relatively intact, e.g., not a plant protoplast lacking cell walls. In embodiments, the plant cell has intact cell walls. In embodiments, the plant cell includes a cell wall that has not been treated by physical (e.g., sonication, abrasion, heating, or chilling), chemical (e.g., treatment with solvents or surfactants), or enzymatic treatments. In embodiments, the plant cell is in its native state, for example, a plant cell that has a cell wall that has not been treated or made porous or permeable by chemical, enzymatic, or physical means. In other embodiments, the plant cell, or a tissue containing the plant cell, is provided in a composition further including at least one reagent, or has been pre-treated with at least one reagent, wherein the reagent is one or more selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; saponins or glycosylated triterpenoids or glycosylated sterols (e.g., saponin commercially available as catalogue number 47036-50g-F, Sigma-Aldrich, St. Louis, Mo.); long chain alcohols; organosilicone surfactants including non-ionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot] html and Järver (2012) *Mol. Therapy—Nucleic Acids*, 1:e27, 1-17); octa-arginine or nona-arginine; poly-homoarginine (see Unnamalai et al. (2004) *FEBS Letters*, 566:307-310); see also the database of cell-penetrating peptides CPPsite 2.0 publicly available at crdd[dot]osdd[dot]net/raghava/cpp-site/(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.*, 39:5284-5298), Transit® transfection reagents (Minis Bio, LLC, Madison, Wis.), and poly-lysine, poly-homoarginine, and poly-arginine molecules including octo-arginine and nono-arginine as described in Lu et al. (2010) *J Agric. Food Chem.*, 58:2288-2294);

(n) antibiotics, including non-specific DNA double-strand-break-inducing agents (e.g., phleomycin, bleomycin, talisomycin);

(o) antioxidants (e.g., glutathione, dithiothreitol, ascorbate); and (p) chelating agents (e.g., EDTA, EGTA).

In embodiments, the plant cell, or a tissue containing the plant cell, is provided in a composition including exogenous non-specific DNA (e.g., non-specific double-stranded DNA, non-specific single-stranded DNA, commercially available sheared salmon sperm DNA).

The magnetic particle together with its biological material cargo is accelerated toward a plant cell multiple times, resulting in delivery of the biological material to the interior of the plant cell. In embodiments, the method employs ferromagnetic or superparamagnetic nanoparticles that are accelerated toward a plant cell multiple times (e.g., at least 2, 3, 4, 5, 6, 7, or 8, or even more accelerations) by means of a magnetic field. In an embodiment, the magnetic field is non-oscillating (static). In an embodiment, the magnetic particle is accelerated toward a plant cell multiple times by consecutive applications of a magnetic field interspersed with withdrawal of the magnetic field. In an embodiment, the plant cell, while in contact with a liquid composition containing the magnetic particle, is treated by repeated placement in proximity to, and then separation from, a permanent magnet. In an embodiment, the magnetic field is provided by a permanent magnet, e.g., a rare-earth magnet or magnetized iron-alloy magnet. Embodiments include the "Super Magnetic Plate" and "Mega Magnetic Plate" available from OZ Biosciences (San Diego, Calif.), which are designed for use with multi-well culture dishes. In an embodiment, the magnet is an electromagnet. In an embodiment, a magnetic field is generated and then discontinued repeatedly in order to accelerate the magnetic particle toward the plant cell.

In specific embodiments, an exogenous biological material including a sequence-specific genome editing agent, such as a sequence-specific nuclease (or a polynucleotide encoding such a sequence-specific nuclease), is delivered to a plant cell located in a pollen grain, and at least one non-random genomic modification is effected by the sequence-specific genome editing agent in the plant cell. By "non-random genomic modification" is meant at least one nucleotide is inserted, deleted, or changed at a sequence-specific location within a pre-selected genomic locus. As is known in the art, the sequence-specific genome editing agent is directed to the pre-selected genomic locus by sequence-specificity, e.g., by selecting the correct guide RNA sequence to direct a Cas nuclease to the pre-selected genomic locus; the non-random genomic modification is then effected specifically at that locus. In an embodiment, a ribonucleoprotein including a Cas nuclease and guide RNA, optionally with a donor polynucleotide, is delivered to a male gamete or male reproductive cell located in a pollen grain. In embodiments, the plant cell is a generative cell or a tube cell located in a pollen grain, and the method further includes the step of germinating the pollen grain. In some embodiments, the method further includes the steps of germinating the pollen grain to form a pollen tube, and contacting the resulting pollen tube with female reproductive tissue or female gametes of a maternal plant, thereby resulting in fertilization of an egg of the maternal plant. In some embodiments, the plant cell is a generative cell located in a pollen grain, and the method further includes the steps of germinating the pollen grain to form a pollen tube and contacting the resulting pollen tube with a stigma, stigma style, ovary, or ovum of a maternal plant, thereby resulting in fertilization of an egg of the maternal plant; in certain of these embodiments, the biological material includes a sequence-specific genome editing agent that effects a non-random genomic modification in the generative cell, and the zygote produced by the fertilization includes the non-random modification in its genome. In some embodiments, the plant cell is a tube cell located in a pollen grain, and the method further includes the steps of germinating the pollen grain and contacting the resulting pollen tube with a stigma, stigma style, ovary, or ovum of a maternal plant, thereby resulting in fertilization of an egg of the maternal plant; in certain of these embodiments, the biological material includes a sequence-specific genome editing agent, and the zygote produced by the fertilization includes a non-random modification in its genome, wherein the non-random genomic modification is effected by the sequence-specific genome editing agent. Thus, a related aspect of this disclosure provides a method of producing a plant zygote including in its genome an inherited, non-random genomic modification, wherein the non-random genomic modification is inherited from a parent germinative cell that gave rise to the zygote, and wherein the non-random genomic modification was effected in the parent germinative cell by an exogenously provided sequence-specific nuclease (or a polynucleotide encoding such a sequence-specific nuclease) non-covalently linked to a magnetic particle. In embodiments, no selection (e.g., no use of antibiotics or herbicides) is employed in the method.

Related aspects of this disclosure include the plant cell into which the exogenous biological material has been delivered (e.g., a plant cell in which a genomic modification has been effected by an exogenous sequence-specific genome editing agent that was delivered using the disclosed method), as well as progeny plant cells, tissue, plants, or seeds grown from or regenerated from the plant cell. In general, the method described here results in fertile regenerated plantlets, e.g., fertile tomato plantlets or fertile soybean plantlets. In embodiments the method provides fertile plantlets including germline cells having at least one non-random genetic modification, in comparison to an unmodified control genome, wherein the at least one non-random genetic modification was effected by the exogenous biological material. In embodiments, the germline cells having at least one non-random genetic modification can give rise to further generations of seeds and plants that also contain the at least one genetic modification in their genome.

Method of Providing a Genome Editing Agent to a Plant Cell

This disclosure provides a method of providing a genome editing agent to a plant cell, comprising multiple applications of a magnetic field to a composition including (a) a plant tissue containing a plant cell; and (b) magnetic nanoparticles of about 150 to about 300 nanometers in diameter that are non-covalently complexed with a genome editing agent; whereby the genome editing agent is delivered to the interior of the plant cell. In embodiments, the method results in a non-random genomic modification of the plant cell.

In embodiments, the plant cell includes a cell wall that has not been treated by physical (e.g., sonication, abrasion, heating, or chilling), chemical (e.g., treatment with solvents or surfactants), or enzymatic treatments. In embodiments, the plant cell is in its native state, for example, a plant cell that has a cell wall that has not been treated or made porous or permeable by chemical, enzymatic, or physical means. In embodiments, the plant cell is a cell of a dicot plant. In other embodiments, the plant cell is a cell of a monocot plant. In embodiments, the plant cell is located in a plant tissue, such as in at least one plant tissue selected from the group consisting of an intact nodal bud, a shoot apex or shoot apical meristem, a root apex or root apical meristem, lateral meristem, intercalary meristem, a seedling (e.g., a germinating seed or small seedling or a larger seedling with one or more true leaves), leaf tissue, a whole seed (e.g., an intact seed, or a seed with part or all of its seed coat removed or treated to make permeable), a halved seed or other seed fragment, an embryo (e.g., a mature dissected zygotic embryo, a developing embryo, a dry or rehydrated or freshly excised embryo) or embryonic tissue, an anther, a stigma, a style, an ovule, an ovary, and callus. In embodiments, the plant cell is in pollen (i.e., in a pollen grain). In embodiments, the plant cell is in a pre-hydrated pollen grain. In embodiments, the plant cell is located in a pre-anthesis pollen grain. In embodiments, the plant cell is located in a pre-anthesis-stage dicot pollen grain. In a specific embodiment, the plant cell is from a soybean plant and is located in a pre-anthesis-stage soybean pollen grain. In embodiments, the plant cell is haploid. In embodiments, the plant cell is a cell of a haploid inducer plant, such as a cell in a pollen grain of a haploid inducer plant. The method can also be used with individual plant cells (i.e., not in a tissue), such as plant cells in suspension (e.g., cultured plant cells in liquid medium) or fixed onto a solid surface or matrix. In embodiments, the plant cell, or a tissue containing the plant cell, is provided in a composition including exogenous non-specific DNA (e.g., non-specific double-stranded DNA, non-specific single-stranded DNA, commercially available sheared salmon sperm DNA).

In embodiments, the genome editing agent is selected from the group consisting of sequence-specific nucleases or polynucleotides encoding such nucleases, or ribonucleoproteins including a sequence-specific nuclease. In embodiments, the genome editing agent is at least one selected from (a) a polynucleotide selected from the group consisting of an RNA guide for an RNA-guided nuclease, a DNA encoding an RNA guide for an RNA-guided nuclease; (b) a nuclease selected from the group consisting of an RNA-guided nuclease, an RNA-guided DNA endonuclease, a type I Cas nuclease, a type II Cas nuclease, Cas9, a type V Cas nuclease, Cas12a (Cpf1), CasY, CasX, C2c1, C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (c) a polynucleotide encoding one or more nucleases (e.g., those enumerated in (b)) capable of effecting site-specific alteration of a target nucleotide sequence. In embodiments, the genome editing agent includes a polypeptide (such as a sequence-specific nuclease) having a sequence that is codon-optimized for the plant (dicot or monocot), as is best suited. See also the paragraphs captioned "Genome Editing Agents" in the "Related Disclosure" section of this disclosure. In embodiments, the method is useful for providing to a plant cell polynucleotides encoding sequence-specific genome editing agents, such as DNA encoding base editors or DNA encoding Cas nucleases and associated guide RNAs and donor polynucleotides. In embodiments, the genome editing agent includes a polynucleotide (e.g., DNA, RNA, or a combination of DNA and RNA), which can be isolated from a natural source, or synthetically produced; such polynucleotides can be chemically or biochemically modified, e.g., to improve stability or solubility. In embodiments, the genome editing agent consists essentially of one or more polynucleotides but includes no protein. In other embodiment, the genome editing agent includes a polypeptide (e.g., a Cas nuclease) or a ribonucleoprotein (e.g., a Cas nuclease's associated guide RNA and optional donor polynucleotide); such polypeptides can be chemically or biochemically modified, e.g., to incorporate a fluorescent label, a nuclear localization signal (NLS), or a cell-penetrating peptide (CPP). In embodiments, the genome editing agent includes a ribonucleoprotein including a Cas nuclease and its associated guide RNA, a guide RNA, and a donor polynucleotide; or one or more polynucleotides encoding such. In embodiments, the genome editing agent includes a sequence-specific genome editing agent, such as a deactivated sequence-specific nuclease (e.g., a "dead" Cas nuclease), which can be complexed with other polypeptides (e.g., polypeptides including a functional domain) or with polynucleotides or with both.

The magnetic nanoparticles are non-covalently complexed with a genome editing agent. In embodiments, the method employs ferromagnetic or superparamagnetic nanoparticles. In embodiments, the magnetic particle is approximately spherical, i.e., the dimensions are approximately equal in all directions, unlike a particle shaped like a rod, tube, or needle. In embodiments, the magnetic particle is an approximately spherical magnetic nanoparticle of about 150 to about 300 nanometers in diameter. In embodiments, the magnetic nanoparticle is surface-modified, e.g., to modify the average charge or polarity on the nanoparticle's surface. In embodiments, the magnetic particle is a nanoparticle comprising iron oxides (e.g., PolyMag or PolyMag Neo reagents, available from OZ Biosciences, Inc., San Diego, Calif.). In embodiments, the magnetic particle is a nanoparticle comprising iron oxides mixed with or coated with a synthetic polymer, such as polyethyleneimine. In embodiments, the magnetic particle is a nanoparticle comprising a gold-coated iron oxide core or "magnetic core gold nanoshell" (e.g., "Magnetic 150 nm Gold Nanoshells" or "Magnetic 280 nm Gold Nanoshells", available from nanoComposix, Inc., San Diego, Calif.), which are optionally surface-modified (e.g., with carboxyl groups).

In embodiments, the composition is a liquid suspension containing the plant tissue and the magnetic nanoparticles. In embodiments, the composition includes exogenous non-specific DNA (e.g., non-specific double-stranded DNA, non-specific single-stranded DNA, commercially available sheared salmon sperm DNA). In an embodiment, the composition includes exogenous non-specific DNA at a concentration of between 0.05-1 milligrams per microliter; in a specific embodiment, the composition includes exogenous non-specific DNA at a concentration of between 0.1-0.5 milligrams per microliter. In a specific embodiment, a magnetic field provided by a permanent magnet is applied multiple (e.g., 2, 3, 4, 5, 6, 7, 8, 9, or 10) times to a composition including (a) a dicot pollen grain in a solution including exogenous non-specific DNA of an average size of ≤2,000 bp (e.g., UltraPure™ Salmon Sperm DNA Solution (Invitrogen™), catalogue number 15632011, Thermo Fisher Scientific, Waltham, Mass.) at a concentration of between 0.1-0.5 milligrams per microliter; and (b) magnetic nanoparticles of about 150 to about 300 nanometers in diameter that are non-covalently complexed with a ribonucleoprotein (RNP) including a Cas nuclease and a guide RNA; whereby the RNP is delivered to the interior of the plant cell.

In embodiments, the method results in a non-random genomic modification of the plant cell. In a specific embodiment, the plant cell is from a soybean plant and is located in a pre-anthesis-stage soybean pollen grain. In embodiments, the plant cell is haploid. In embodiments, the plant cell is a cell of a haploid inducer plant, such as a cell in a pollen grain of a haploid inducer plant. The method can also be used with individual plant cells (i.e., not in a tissue), such as plant cells in suspension (e.g., cultured plant cells in liquid medium) or fixed onto a solid surface or matrix. In embodiments, the plant cell, or a tissue containing the plant cell, is provided in a composition including exogenous non-specific DNA (e.g., non-specific double-stranded DNA, non-specific single-stranded DNA, commercially available sheared salmon sperm DNA).

In other embodiments, the composition further includes at least one reagent selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; saponins or glycosylated triterpenoids or glycosylated sterols (e.g., saponin commercially available as catalogue number 47036-50g-F, Sigma-Aldrich, St. Louis, Mo.); long chain alcohols; organosilicone surfactants including non-ionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides;

gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot] html and Järver (2012) *Mol. Therapy—Nucleic Acids*, 1:e27, 1-17); octa-arginine or nona-arginine; poly-homoarginine (see Unnamalai et al. (2004) *FEBS Letters*, 566:307-310); see also the database of cell-penetrating peptides CPPsite 2.0 publicly available at crdd[dot]osdd[dot]net/raghava/cppsite/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), PepFect (see Ezzat et al. (2011) *Nucleic Acids Res.*, 39:5284-5298), Transit® transfection reagents (Mirus Bio, LLC, Madison, Wis.), and poly-lysine, poly-homoarginine, and poly-arginine molecules including octo-arginine and nono-arginine as described in Lu et al. (2010) *J. Agric. Food Chem.*, 58:2288-2294);

(n) antibiotics, including non-specific DNA double-strand-break-inducing agents (e.g., phleomycin, bleomycin, talisomycin);

(o) antioxidants (e.g., glutathione, dithiothreitol, ascorbate); and (p) chelating agents (e.g., EDTA, EGTA).

In embodiments, the method results in a non-random genomic modification of the plant cell. By "non-random genomic modification" is meant at least one nucleotide is inserted, deleted, or changed at a sequence-specific location within a pre-selected genomic locus. As is known in the art, the genome editing agent is directed to the pre-selected genomic locus by sequence-specificity, e.g., by selecting the correct guide RNA sequence to direct a Cas nuclease to the pre-selected genomic locus; the non-random genomic modification is then effected specifically at that locus. In embodiments, the plant cell is a generative cell in a pollen grain (e.g., a pre-hydrated dicot pollen grain) and the method results in a non-random genomic modification of the male generative cell (sperm cell) which is heritable to zygotes resulting from pollination by that male generative cell. In embodiments, the method results in delivery of the genome editing agent to a pollen grain, and a subsequent delivery of the genome editing agent to a female generative cell via a pollen tube formed by the pollen grain; in such a situation, the method results in a non-random genomic modification of the female generative cell (egg cell) which is heritable to zygotes resulting from pollination by that female generative cell. Thus, a related aspect of this disclosure provides a method of producing a plant zygote including in its genome an inherited, non-random genomic modification, wherein the non-random genomic modification is inherited from a parent germinative cell that gave rise to the zygote, and wherein the non-random genomic modification was effected in the parent germinative cell by an exogenously provided genome editing agent (or a polynucleotide encoding such a genome editing agent) non-covalently linked to a magnetic particle.

Related aspects of this disclosure include the plant cell into which the genome editing agent has been delivered (e.g., a plant cell in which a genomic modification has been effected by an exogenous sequence-specific genome editing agent that was delivered using the disclosed method), as well as progeny plant cells, tissue, plants, or seeds grown from or regenerated from the plant cell. In general, the method described here results in fertile regenerated plantlets, e.g., fertile tomato plantlets or fertile soybean plantlets. In embodiments the method provides fertile plantlets including germline cells having at least one non-random genetic modification, in comparison to an unmodified control genome, wherein the at least one non-random genetic modification was effected by the genome editing agent. In embodiments, the germline cells having at least one non-random genetic modification can give rise to further generations of seeds and plants that also contain the at least one genetic modification in their genome.

Plant Modification Systems

Further provided by this disclosure is a plant modification system including: (a) a sequence-specific nuclease that is non-covalently complexed with an approximately spherical magnetic nanoparticle of about 150 to about 300 nanometers in diameter; (b) a pollen grain; (c) a medium containing exogenous non-specific DNA.

In embodiments, the sequence-specific nuclease is one or more nuclease selected from the group consisting of a Cas nuclease, a zinc finger nuclease, a TAL effector nuclease (TALEN), and an Argonaute. In embodiments, the sequence-specific nuclease is provided as a polypeptide (or as a ribonucleoprotein, if further including a guide RNA and optionally a donor polynucleotide). In embodiments, the sequence-specific nuclease is a Cas nuclease. In embodiments, the sequence-specific nuclease is a Cas nuclease provided as a ribonucleoprotein that includes at least one guide RNA and further is provided together with at least one donor polynucleotide. In embodiments, the sequence-specific nuclease (and optionally a guide RNA and/or donor polynucleotide) is provided encoded on a polynucleotide, such as on a plasmid vector, with expression driven by a promoter suitable to the plant species (e.g., a 35S promoter, half-strength 35S promoter, SlUbi promoter, Lat52 promoter, etc.). In embodiments, the sequence-specific nuclease is deactivated ("dead") and can bind to but not cleave the targeted genomic locus; in certain embodiments such cases the sequence-specific nuclease is complexed with or fused to one or more additional functional domains. See also the paragraphs captioned "Genome Editing Agents" in the "Related Disclosure" section of this disclosure. In embodiments, the sequence-specific nuclease is codon-optimized for the plant (dicot or monocot), as is best suited.

The plant modification system includes an approximately spherical magnetic nanoparticle that is about 150 to about 300 nanometers in diameter. In embodiments, the method employs ferromagnetic or superparamagnetic nanoparticles. In embodiments, the magnetic particle is approximately spherical, i.e., the dimensions are approximately equal in all directions, unlike a particle shaped like a rod, tube, or needle. In embodiments, the magnetic particle is an approximately spherical ferromagnetic nanoparticle of about 150 to about 300 nanometers in diameter. In embodiments, the magnetic nanoparticle is surface-modified, e.g., to modify the average charge or polarity on the nanoparticle's surface. In embodiments, the magnetic particle is a nanoparticle comprising iron oxides (e.g., PolyMag or PolyMag Neo reagents, available from OZ Biosciences, Inc., San Diego, Calif.). In embodiments, the magnetic particle is a nanoparticle comprising iron oxides mixed with or coated with a synthetic polymer, such as polyethyleneimine. In embodiments, the magnetic particle is a nanoparticle comprising a gold-coated iron oxide core or "magnetic core gold nanoshell" (e.g., "Magnetic 150 nm Gold Nanoshells" or "Magnetic 280 nm Gold Nanoshells", available from nanoComposix, Inc., San Diego, Calif.), which are optionally surface-modified (e.g., with carboxyl groups).

The plant modification system includes a pollen grain. In embodiments, the pollen grain is pre-hydrated before addition to the plant modification system; in other embodiments, the pollen grain is not pre-hydrated before addition to the plant modification system. In embodiments, the pollen grain is located in a pre-anthesis pollen grain. In embodiments, the pollen grain is a pre-anthesis-stage dicot pollen grain. In an embodiment, the pollen grain is from a soybean plant. In a specific embodiment, the pollen grain is a pre-anthesis-stage soybean pollen grain. In embodiments, the pollen grain is a pollen grain of a haploid inducer plant.

The plant modification system further includes a medium containing exogenous non-specific DNA. The medium is generally a liquid medium. In an embodiment, the medium includes exogenous non-specific DNA at a concentration of between 0.05-1 milligrams per microliter. In an embodiment, the medium includes exogenous non-specific DNA at a concentration of between 0.1-0.5 milligrams per microliter. In an embodiment, the exogenous non-specific DNA is of an average size of ≤2,000 bp (e.g., UltraPure™ Salmon Sperm DNA Solution (Invitrogen™), catalogue number 15632011, Thermo Fisher Scientific, Waltham, Mass.). In an embodiment, the plant modification system includes a medium containing exogenous non-specific DNA of an average size of ≤2,000 bp at a concentration of between 0.1-0.5 milligrams per microliter. In a specific embodiment, the plant modification system includes (a) a sequence-specific nuclease, such as a Cas nuclease or a ribonucleoprotein (RNP) including a Cas nuclease and a guide RNA, that is non-covalently complexed with an approximately spherical magnetic nanoparticle of about 150 to about 300 nanometers in diameter; (b) a dicot pollen grain; (c) a medium containing exogenous non-specific DNA of an average size of ≤2,000 bp at a concentration of between 0.1-0.5 milligrams per microliter; in embodiments, the system further includes a non-oscillating (static) magnetic field such as a magnetic field provided by a permanent magnet. In embodiments, the medium further includes at least one reagent selected from the group consisting of:

(a) solvents (e.g., water, dimethylsulfoxide, dimethylformamide, acetonitrile, N-pyrrolidine, pyridine, hexamethylphosphoramide, alcohols, alkanes, alkenes, dioxanes, polyethylene glycol, and other solvents miscible or emulsifiable with water or that will dissolve phosphonucleotides in non-aqueous systems);

(b) fluorocarbons (e.g., perfluorodecalin, perfluoromethyldecalin);

(c) glycols or polyols (e.g., propylene glycol, polyethylene glycol);

(d) surfactants, including cationic surfactants, anionic surfactants, non-ionic surfactants, and amphiphilic surfactants, e.g., alkyl or aryl sulfates, phosphates, sulfonates, or carboxylates; primary, secondary, or tertiary amines; quaternary ammonium salts; sultaines, betaines; cationic lipids; phospholipids; tallowamine; bile acids such as cholic acid; saponins or glycosylated triterpenoids or glycosylated sterols (e.g., saponin commercially available as catalogue number 47036-50g-F, Sigma-Aldrich, St. Louis, Mo.); long chain alcohols; organosilicone surfactants including non-ionic organosilicone surfactants such as trisiloxane ethoxylate surfactants or a silicone polyether copolymer such as a copolymer of polyalkylene oxide modified heptamethyl trisiloxane and allyloxypolypropylene glycol methylether (commercially available as SILWET L-77™ brand surfactant having CAS Number 27306-78-1 and EPA Number CAL. REG. NO. 5905-50073-AA, Momentive Performance Materials, Inc., Albany, N.Y.); specific examples of useful surfactants include sodium lauryl sulfate, the Tween series of surfactants, Triton-X100, Triton-X114, CHAPS and CHAPSO, Tergitol-type NP-40, Nonidet P-40;

(e) lipids, lipoproteins, lipopolysaccharides;

(f) acids, bases, caustic agents;

(g) peptides, proteins, or enzymes (e.g., cellulase, pectolyase, maceroenzyme, pectinase), including cell-penetrating or pore-forming peptides (e.g., (BO100)2K8, Genscript; poly-lysine, poly-arginine, or poly-homoarginine peptides; gamma zein, see US Patent Application publication 2011/0247100, incorporated herein by reference in its entirety; transcription activator of human immunodeficiency virus type 1 ("HIV-1 Tat") and other Tat proteins, see, e.g., www[dot]lifetein[dot]com/Cell_Penetrating_Peptides[dot]html and Järver (2012) *Mol. Therapy—Nucleic Acids*, 1:e27, 1-17); octa-arginine or nona-arginine; poly-homoarginine (see Unnamalai et al. (2004) *FEBS Letters*, 566:307-310); see also the database of cell-penetrating peptides CPPsite 2.0 publicly available at crdd[dot]osdd[dot]net/raghava/cpp-site/

(h) RNase inhibitors;

(i) cationic branched or linear polymers such as chitosan, poly-lysine, DEAE-dextran, polyvinylpyrrolidone ("PVP"), or polyethylenimine ("PEI", e.g., PEI, branched, MW 25,000, CAS #9002-98-6; PEI, linear, MW 5000, CAS #9002-98-6; PEI linear, MW 2500, CAS #9002-98-6);

(j) dendrimers (see, e.g., US Patent Application Publication 2011/0093982, incorporated herein by reference in its entirety);

(k) counter-ions, amines or polyamines (e.g., spermine, spermidine, putrescine), osmolytes, buffers, and salts (e.g., calcium phosphate, ammonium phosphate);

(l) polynucleotides (e.g., non-specific double-stranded DNA, salmon sperm DNA);

(m) transfection agents (e.g., Lipofectin®, Lipofectamine®, and Oligofectamine®, and Invivofectamine® (all from Thermo Fisher Scientific, Waltham, Mass.), Pep-Fect (see Ezzat et al. (2011) *Nucleic Acids Res.*, 39:5284-5298), Transit® transfection reagents (Mirus Bio, LLC, Madison, Wis.), and poly-lysine, poly-homoarginine, and poly-arginine molecules including octo-arginine and nono-arginine as described in Lu et al. (2010) *J. Agric. Food Chem.*, 58:2288-2294);

(n) antibiotics, including non-specific DNA double-strand-break-inducing agents (e.g., phleomycin, bleomycin, talisomycin);

(o) antioxidants (e.g., glutathione, dithiothreitol, ascorbate); and (p) chelating agents (e.g., EDTA, EGTA).

In embodiments, the plant modification system, further includes a magnet that provides a magnetic field. In embodiments, the magnet provides a non-oscillating magnetic field. In an embodiment, the magnet is a permanent magnet, e.g., a rare-earth magnet or magnetized iron-alloy magnet.

Embodiments include the "Super Magnetic Plate" and "Mega Magnetic Plate" available from OZ Biosciences (San Diego, Calif.), which are designed for use with multi-well culture dishes. In an embodiment, the magnet is an electromagnet. In an embodiment, the magnet provides a magnetic field that is generated and then discontinued repeatedly, resulting in multiple accelerations of the magnetic nanoparticle toward the pollen grain.

Related Disclosure

Plants of Interest:

The methods, compositions, and systems disclosed herein are useful in effecting a non-random genetic modification in a monocot plant or in a dicot plant. The method is of use particularly in effecting a non-random genetic modification in dicot plants, such as, but not limited to, leguminous plants (e.g., soybean) or solanaceous plants (e.g., tomato, pepper), including dicot plants of elite germplasm or of inbred lines. In embodiments, the methods, compositions, and systems disclosed herein are employed to effect non-random genetic modifications in cultivated plants, including those of inbred varieties or "elite" germplasm. Non-limiting examples of commercially important cultivated crops, trees, and plants include: alfalfa (*Medicago sativa*), almonds (*Prunus dulcis*), apples (*Malus×domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinum* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus xparadisi*), grapes (*Vitus* spp.) including wine grapes (*Vitus vinifera*), guava (*Psidium guajava*), hops (*Humulus lupulus*), hemp and *cannabis* (*Cannabis sativa* and *Cannabis* spp.), irises (Iris spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (Sesame indium), sorghum (*Sorghum bicolor*), soybean (*Glycine max* L.), squash (*Cucurbita pepo*), strawberries (*Fragaria* spp., *Fragaria×ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.).

Recombinant Constructs and Vectors:

Plasmids designed for use in plants and encoding CRISPR genome editing elements (CRISPR nucleases and guide RNAs) are publicly available from plasmid repositories such as Addgene (Cambridge, Mass.; also see "addgene[dot] com") or can be designed using publicly disclosed sequences, e.g., sequences of CRISPR nucleases. In embodiments, such plasmids are used to co-express both a CRISPR nuclease mRNA and guide RNA(s); in other embodiments, a CRISPR nuclease mRNA and guide RNA are encoded on separate plasmids. In embodiments, the plasmids contain left and right T-DNA borders, e.g., *Agrobacterium* TI (Ti) plasmids. Materials and methods for preparing expression cassettes and vectors for CRISPR endonuclease and guide RNA for use in genetic modification of plants are disclosed in PCT/US2015/018104 (published as WO/2015/131101 and claiming priority to U.S. Provisional Patent Application 61/945,700), US Patent Application Publication 2015/0082478 A1, and PCT/US2015/038767 (published as WO/2016/007347 and claiming priority to U.S. Provisional Patent Application 62/023,246), all of which are incorporated herein by reference in their entirety. In embodiments, the expression cassette is adjacent to or located between T-DNA borders or contained within a binary vector, e.g., a binary vector that is compatible with *Agrobacterium*-mediated transformation. In other embodiments, the expression cassette does not include a T-DNA border. In embodiments, the transformation construct of the methods and systems disclosed herein includes (a) DNA encoding a CRISPR nuclease and (b) DNA encoding one or multiple guide RNAs; the transformation construct optionally includes DNA encoding one or more donor polynucleotides.

Genome Editing Agents:

Embodiments of genome editing agents include: (a) a polynucleotide selected from the group consisting of an RNA guide for an RNA-guided nuclease, a DNA encoding an RNA guide for an RNA-guided nuclease; (b) a sequence-specific nuclease selected from the group consisting of an RNA-guided nuclease, an RNA-guided DNA endonuclease, a type II Cas nuclease, a Cas9, a type V Cas nuclease, a Cpf1, a CasY, a CasX, a C2c1, a C2c3, an engineered nuclease, a codon-optimized nuclease, a zinc-finger nuclease (ZFN), a transcription activator-like effector nuclease (TAL-effector nuclease), Argonaute, a meganuclease or engineered meganuclease; or (c) a polynucleotide encoding one or more nucleases capable of effecting sequence-specific alteration of a target nucleotide sequence. Any of these nucleases can be codon-optimized, e.g., plant-codon-optimized to function optimally in a plant cell. In embodiments, one or multiple effector molecules are delivered individually (e.g., in separate compositions) or in combinations (e.g., in a ribonucleoprotein), and in a single step or multiple steps.

Zinc finger nucleases (ZFNs) are engineered proteins including a zinc finger DNA-binding domain fused to a nucleic acid cleavage domain, e.g., a nuclease. The zinc finger binding domains provide sequence specificity and can be engineered to specifically recognize any desired target DNA sequence. For a review of the construction and use of ZFNs in plants and other organisms, see, e.g., Urnov et al. (2010) *Nature Rev. Genet.*, 11:636-646. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotides bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) are well known and described in the literature. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described; see, e.g., Guo et al. (2010) *J. Mol. Biol.*, 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and sequence-specific DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. For a description of the use of TALENs in plants, see Mahfouz et al. (2011) *Proc. Natl. Acad. Sci. USA,* 108:2623-2628 and Mahfouz (2011) *GM Crops,* 2:99-103.

Argonautes are proteins that can function as sequence-specific endonucleases by binding a polynucleotide (e.g., a single-stranded DNA or single-stranded RNA) that includes sequence complementary to a target nucleotide sequence) that guides the Argonaut to the target nucleotide sequence and effects site-specific alteration of the target nucleotide sequence; see, e.g., US Patent Application Publication 2015/0089681, incorporated herein by reference in its entirety.

In related embodiments, sequence-specific nucleases such as Cas nucleases, zinc finger nucleases, TALENs, and Argonautes are used in conjunction with other functional domains. For example, the sequence-specific nuclease activity of these nucleic acid targeting systems can be altered so that the enzyme specifically binds to but does not cleave the target DNA sequence. In embodiments, the sequence-specific nuclease is deactivated ("dead") and can bind to but not cleave the targeted genomic locus; in certain embodiments such cases the (deactivated) sequence-specific nuclease is complexed with or fused to one or more additional functional domains. Embodiments include a deactivated sequence-specific nuclease (e.g., a "dead" Cas nuclease), which can be complexed with other polypeptides (e.g., polypeptides including a functional domain) or with polynucleotides or with both. In embodiments, an active sequence-specific nuclease is non-covalently or covalently complexed with at least one polypeptide containing a functional domain. Examples of functional domains include transposase domains, integrase domains, recombinase domains, resolvase domains, invertase domains, protease domains, DNA methyltransferase domains, DNA hydroxylmethylase domains, DNA demethylase domains, histone acetylase domains, histone deacetylase domains, nuclease domains, repressor domains, activator domains, nuclear-localization signal domains, transcription-regulatory protein (or transcription complex recruiting) domains, cellular uptake activity associated domains, nucleic acid binding domains, antibody presentation domains, histone modifying enzymes, recruiter of histone modifying enzymes; inhibitor of histone modifying enzymes, histone methyltransferases, histone demethylases, histone kinases, histone phosphatases, histone ribosylases, histone deribosylases, histone ubiquitinases, histone deubiquitinases, histone biotinases and histone tail proteases. Non-limiting examples of functional domains include a transcriptional activation domain, a transcription repression domain, and an SEIM, SUVH2, or SUVH9 polypeptide capable of reducing expression of a target nucleotide sequence via epigenetic modification; see, e.g., US Patent Application Publication 2016/0017348, incorporated herein by reference in its entirety. Genomic DNA may also be modified via base editing using a fusion between a catalytically inactive "dead" Cas nuclease (dCas nuclease) is fused to a nucleobase editor, for example, a dCas9 nuclease is fused to a cytidine deaminase which converts cytosine (C) to uridine (U), thereby effecting a C to T substitution; see Komor et al. (2016) *Nature,* 533:420-424.

EXAMPLES

Example 1

This example illustrates several embodiments of media useful in the methods and systems described herein. Tables 1-5 provide non-limiting examples of various media formulations suitable for use in the sequence-specific plant genome modification methods and systems described herein.

TABLE 1 tomato pollen germination medium (liquid)

| Stock solution | Stock concentration | To make 5 mL |
|---|---|---|
| PEG 4000 | 40% | 3 |
| Boric acid | 0.1% | 0.5 |
| Sucrose | 40% | 0.25 |
| HEPES buffer | 0.5M, pH 6.0 | 0.2 |
| $Ca(NO_3)_2 \cdot 4H_2O$ | 0.1M | 0.15 |
| $MgSO_4 \cdot 7H_2O$ | 2% | 0.05 |
| $KNO_3$ | 1% or 0.1M | 0.05 |
| $H_2O$ | Double distilled | 0.8 |

TABLE 2 tomato pollen germination medium (solid)

| Component | Amount |
|---|---|
| Boric Acid | 50 mg/L |
| Sucrose | 10% |
| agar | 0.5% |

TABLE 3 tomato pollen culture medium (liquid)

| Component | 1 | 2 | 3 | 4 | 5 |
|---|---|---|---|---|---|
| Sucrose (g) | 15.0 | 15.0 | 20.0 | 20.0 | 20.0 |
| $H_3BO_3$ (mg) | 7.72 | 10.3 | 10.3 | 10.3 | 7.72 |
| $KNO_3$ (mg) | 5.3 | 5.3 | 5.3 | 5.3 | 5.3 |
| $Ca(NO_3)_2$ (mg) | 10.3 | 10.3 | 10.3 | 10.3 | 10.3 |
| $MnSO_4$ (mg) | 51.7 | 34.5 | 51.7 | 51.7 | 34.5 |
| $MgSO_4 \cdot 7H_2O$ (mg) | 10.3 | 10.3 | 10.3 | 10.3 | 10.3 |
| Gibberellic acid (GA3) (mg) | — | 3.0 | 3.0 | — | — |

*Double-distilled water is added to make 20.0 milliliters of medium

TABLE 4

Maize pollen germination medium

| Component | Formula | | | | | |
|---|---|---|---|---|---|---|
| | 1 | 2 | 3 | 4 | 5 | 6 |
| Sucrose (%) | 5 | 10 | 10 | 15 | 15 | 10 |
| $H_3BO_3$ (%) | 0.0025 | 0.005 | 0.01 | 0.01 | 0.01 | 0.01 |
| $CaCl_2$ (millimolar) | 5 | 10 | 10 | — | — | — |
| $KH_2PO_4$ (millimolar) | 0.025 | 0.05 | 0.05 | — | 0.025 | — |
| $Ca(NO_3)_2$ (%) | — | — | — | 0.025 | 0.025 | 0.025 |
| PEG 4000 (%) | 3 | 6 | — | — | — | — |
| Agar* (%) | 0.3 | 0.3 | 0.3 | 0.6 | 0.6 | 0.6 |

*optional; added for solid medium formulations

TABLE 5 soybean pollen germination medium*

| Component | Formula | | | | | | | | | |
|---|---|---|---|---|---|---|---|---|---|---|
| | 1 | 2 | 3 | 4 | 5 | 6 | 7 | 8 | 9 | 10 |
| Sucrose (g) | 12.5 | 12.5 | 12.5 | 12.5 | 15.0 | 15.0 | 15.0 | 15.0 | 15.0 | 15.0 |
| 0.01% (1.617 mM) $H_3BO_3$ (microliters) | 161.7 | 323.4 | 161.7 | 323.4 | 323.4 | 161.7 | 323.4 | 161.7 | 323.4 | — |
| 0.03% (1.27 mM) $Ca(NO_3)_2 \cdot 4H_2O$ (microliters) | 127 | 127 | 254 | 254 | 254 | 254 | 127 | 127 | — | 254 |

*Double-distilled water is added to make 20.0 milliliters of medium; 0.12 g agar is added for solid medium formulations Example 2

This example illustrates use of a magnetofection protocol including a single acceleration of a polynucleotide non-covalently complexed with a magnetic particle toward a plant cell.

In this example, delivery of DNA plasmids encoding red or green fluorescent reporter proteins to cells in tomato pollen grains was attempted using a magnetofection protocol essentially identical to that reported by Zhao et al. (2017) *Nature Plants*, 3:956-964; including supplementary information available at doi.org/10.1038/s41477-017-0063-z. Pollen was obtained from the tomato (variety Microtom) by dissection of anthers from intact flower and flicking the anthers above a weighing boat, where the pollen grains were collected. The pollen was counted using commercially available hemocytometer slides. The pollen suspension was then adjusted to the approximate concentration of 1 million pollen grains per milliliter of culture media. Pollen grains were transferred to wells of a 96-well plate. Following the protocol of Zhao et al. (2017), 2 microliters of magnetic nanoparticles ("MNPs", PolyMAG cationic polyethylene-imine-modified $Fe_3O_4$ magnetic nanoparticles, Chemicell, Berlin, Germany), vortexed immediately prior to use, were mixed with 8 micrograms of the DNA plasmid of choice (red or green fluorescence, respectively) in a 4:1 DNA:MNP mass ratio; the mixtures were incubated in 1.5 millilitre microfuge tubes for 30 minutes at room temperature (in embodiments, between 15 minutes to 1 hour incubation time is used). One hundred microliters of pollen germination medium (prepared according to Table I or following the formulation for pepper pollen according to Zhao et al. (2017) (i.e., 15 g sucrose, 10.3 mg $H_3BO_3$, 5.3 mg $KNO_3$, 10.3 mg $Ca(NO_3)_2$, 51.7 mg $MnSO_4$, 10.3 mg $MgSO_4.7H_2O$ and 3 mg GA3 in 100 mL water) was added to the DNA:MNP-containing tubes, mixed, and the resulting suspension transferred to the pollen-containing wells. The plate was covered with its lid, and then placed on top of the magnetic array (96-magnet magnetic plate, OZ Biosciences, San Diego, Calif.) for 30 minutes. Following magnetofection, the pollen grain suspension was removed by pipette and the pollen spread on sterile filter paper in culture plates. The plates were sealed with Parafilm and stored in the dark at room temperature to promote germination and plasmid gene expression. No expression of either red or green fluorescence was detected in the magnetofected tomato pollen.

A similar single-acceleration experiment using essentially the same procedures was carried out with a GUS-expressing plasmid and fava bean pollen; no GUS expression was observed with the magnetofected fava bean pollen.

Example 3

This example illustrates use of a magnetofection protocol including multiple accelerations of a magnetic particle toward a plant cell.

Magnetofection experiments were performed on tomato pollen grains with fluorescently-labelled nano-screen MAG-UC/C cationically charged 150 nanometer diameter magnetic nanoparticles (MNPs) (Chemicell, Berlin, Germany) using a protocol modified from that based on Zhao et al. (2017) and described in Example 2. In these experiments, 500,000 tomato pollen grains in 50 microliters tomato pollen culture medium were placed in 2-mL round-bottom tubes, to which was added various amounts (0.25 microliters, 1.25 microliters, or 5 microliters) of the fluorescently labelled MNPs. The tubes were mixed well, then placed on the magnetic plate; every five minutes the tubes were removed from the magnetic field, mixed well, then returned to the magnet; this was repeated over a total time of 7 magnetic accelerations over 30 minutes. The tubes were centrifuged briefly to pellet the pollen grains, the tomato pollen culture medium was replaced with tomato pollen germination medium, and the tubes' contents mixed well and then incubated with shaking at room temperature. Microscope observation showed that the pollen had germinated, producing pollen tubes, and the fluorescent MNPs were observed within the pollen grains and within the pollen tubes.

In contrast, using a single acceleration (placing the pollen/MNP-containing 96-well plate on the magnetic array and incubating 30 minutes in the dark), no clear fluorescent signal was observed in the interior of the pollen grains nor in the pollen tubes (data not shown).

These results indicate that multiple accelerations of the fluorescent MNPs were necessary to transport the fluorescent MNPs into cells in the pollen grains and into the pollen tubes that germinated from the magnetofected pollen grains. These results also demonstrate that the pollen grains retained viability after multiple rounds of MNP acceleration.

Example 4

This example illustrates use of a magnetofection protocol including multiple accelerations of a polynucleotide non-covalently complexed with a magnetic particle toward a plant cell.

An experiment investigating the effects of multiple accelerations of MNPs non-covalently complexed with a biological cargo toward a plant cell was based on the procedures described by Zhao et al. (2017), but instead of the single acceleration of the MNPs toward the plant cell as described by Zhao et al. (2017), multiple accelerations were employed.

PolyMAG cationic polyethyleneimine-modified $Fe_3O_4$ magnetic nanoparticles, Chemicell, Berlin, Germany), vortexed immediately prior to use, were mixed with a DNA plasmid encoding the reporter protein GUS in a 4:1 DNA:MNP mass ratio; the mixture was incubated for 30 minutes at room temperature. Pollen collected from tomato plants (variety M82) was collected, allowed to rehydrate 30 minutes in pepper pollen culture medium (Zhao et al. (2017)), and 150 microliter aliquots (containing 187,500 pollen grains) distributed into microfuge tubes. The DNA:MNP complex was added at the equivalent of 1, 5, or 20 micrograms DNA to groups of 5 replicate tubes; the fourth group of 5 replicate tubes received 5 microliters of MNPs (no DNA plasmid) as a control. The tubes were mixed well, then placed on the magnetic plate; every five minutes the tubes were removed from the magnetic field, mixed well, then returned to the magnet; this was repeated over a total time of 7 magnetic accelerations over 30 minutes. The tubes were centrifuged briefly to pellet the pollen grains, the medium discarded, and the pelleted pollen grains and MNPs resuspended in 1 milliliter tomato pollen germination medium and incubated with shaking at room temperature overnight. All of the pollen germinated well. The pollen germination medium was removed and replaced by GUS staining solution, then incubated at room temperature in the dark overnight. GUS expression was observed in all of the pollen treatments except for the control. These results indicate that multiple accelerations of the MNPs successfully transported the DNA plasmid into cells in the magnetofected pollen grains and the plasmid expressed the GUS protein in the cells.

Additional experiments were performed to validate the method. Different magnetic nanoparticles were tested: PolyMAG cationic polyethyleneimine-modified $Fe_3O_4$ magnetic nanoparticles, Chemicell, Berlin, Germany), PolyMag Neo (OZ Biosciences, San Diego, Calif.) and FluoMag (OZ Biosciences, San Diego, Calif.). The MNPs were vortexed immediately prior to use, and then mixed with a DNA plasmid encoding the reporter protein GUS in a 4:1 DNA:MNP mass ratio; the mixture was incubated for 30 minutes at room temperature. Pollen collected from tomato plants (varieties M82 and Microtom) was collected separately, allowed to rehydrate 30 minutes in pepper pollen culture medium (Zhao et al. (2017)), and 200 microliter aliquots (containing 200,000 pollen grains) distributed into microfuge tubes. The Microtom pollen was magnetofected with PolyMag (OZ Biosciences) or FluoMag MNPs and the M82 pollen magnetofected with PolyMag (Chemicell) MNPs; each DNA:MNP complex was added at the equivalent of 1, 5, or 20 micrograms DNA to sets of duplicate tubes; pairs of duplicate tubes received 5 microliters of MNPs (no DNA plasmid) as a control. The tubes were mixed well, then placed on the magnetic plate; every five minutes the tubes were removed from the magnetic field, mixed well, then returned to the magnet; this was repeated over a total time of 7 magnetic accelerations over 30 minutes. The tubes were centrifuged briefly to pellet the pollen grains, most of the medium discarded by decanting, and the pellets left in their open tubes in a sterile hood overnight to further evaporate the medium. The following day, GUS staining solution was added to the tubes and well mixed, the tubes exposed to 1 minute of vacuum, then incubated in the dark at 37 degrees Celsius overnight, followed by two days of incubation at room temperature. GUS expression was observed at this stage in the Microtom pollen magnetofected with PolyMag (OZ Biosciences) or FluoMag MNPs and in the M82 pollen magnetofected with the PolyMag (Chemicell). By the next day, GUS expression was strong in all Microtom and M82 pollen samples except for the negative (MNP only) controls. These results again demonstrate that multiple accelerations of the MNPs successfully transported the DNA plasmid into cells in the magnetofected pollen grains and the plasmid expressed the GUS protein in the cells.

In similar experiments, pollen from maize is collected and magnetofected using multiple accelerations of MNPs toward the pollen grains using procedures similar to those described in this example for tomato pollen. Pollen grains are resuspended in maize pollen germination medium (Example 1) for germination. The results demonstrate that multiple accelerations of the MNPs deliver DNA plasmids encoding a protein into cells in the magnetofected maize pollen grains and the plasmid expresses the encoded protein in the cells.

Example 5

This example illustrates use of a magnetofection protocol including multiple accelerations of magnetic nanoparticles toward a plant cell. This example further demonstrates viability of pollen grains thus magnetofected.

Approximately 4 million tomato pollen grains were suspended and hydrated in tomato pollen culture media. Aliquots of 50 microliters of about 200,000 hydrated pollen grains were transferred to each of ten tubes. To each tube was then added 150 microliters of pollen culture medium and 5 microliters MNPs. Following the procedure described in Example 3, the tubes were mixed well, then placed on the magnetic plate; every five minutes the tubes were removed from the magnetic field, mixed well, then returned to the magnet; this was repeated over a total time of 7 magnetic accelerations over 30 minutes. The tubes were pooled into two groups (five tubes per group): "wet" pollen and "dry" pollen. Tubes were centrifuged 3 minutes at 3000 rpm. All but about 150 microliters of medium was removed from the "wet" pollen tubes. As much of the medium as possible was removed from the "dry" pollen, which was then scraped out of the tube with a metal spatula and placed on filter paper to air-dry. The wet and dry pollen preparations were each used to pollinate five unopened tomato flowers that were surgically opened, with the wet or dry pollen transferred by paintbrush or pipette tip to the stigma and style of the flowers. The hand-pollinated flowers were wrapped in plastic wrap and placed in light. Both the wet and dry magnetofected pollen preparations were observed to produce tomato fruit with viable seed.

Example 6

This example illustrates a method of delivering a biological material to the interior of a plant cell, including accelerating the biological material that is non-covalently complexed with a magnetic particle multiple times toward a plant cell, whereby the biological material is delivered to the interior of the plant cell. In this example, the biological material includes a polypeptide.

Pollen was collected from tomato (variety Supersweet 100 Cherry) as described in Example 2. The pollen was hydrated with tomato pollen culture medium (formula 3 from Table 3) and divided among 8 tubes, each containing 200,000 pollen grains in 200 microliters medium.

Gold magnetic nanoparticles (AuMNPs, 150 nm diameter, purchased from nanoComposix, Inc., San Diego, Calif.) were sonicated for 5 seconds, mixed in a 1:1 ratio with undiluted red fluorescent protein (1 or 2 microliters), or with a 1:10 dilution red fluorescent protein (1, 2, or 3 microliters), and allowed to incubate 5 minutes to form protein:AuMNP complexes before adding to the pollen. (In embodiments, between 15 minutes to 1 hour incubation time is used to non-covalently complex a protein with an MNP; protein:MNP complex formation and stability is assessed by convenient methods such as by Coomassie Blue staining.) Five of the 8 tubes containing hydrated pollen received one of the protein:AuMNP preparations; the 3 remaining tubes served as controls and received 1 microliter AuMNPs with no protein, 1 microliter protein only (no AuMNPs), or nothing. Following the procedure described in Example 3, the tubes were mixed well, then placed on the magnetic plate; every five minutes the tubes were removed from the magnetic field, mixed well, then returned to the magnet; this was repeated over a total time of 7 magnetic accelerations over 30 minutes. After magnetofection, the tubes were centrifuged briefly to pellet the pollen, the pollen culture medium removed and replaced with tomato pollen germination medium (Table 1), and the tubes' contents mixed well.

Microscopic observation showed the red fluorescent protein signal was very strong in the pollen that had been magnetofected with the AuMNP complexed with 1 or 2 microliters of undiluted protein; the fluorescent signal was also seen in the germinating pollen tubes. The red fluorescence signal was also visible, though less bright, in the pollen that had been magnetofected with the AuMNP complexed with 1, 2, or 3 microliters of 1:10 diluted proteins. In all cases the signal was stronger than in pollen treated with red fluorescent protein only (no AuMNPs). The results indicate that multiple accelerations of the AuMNPs successfully transported a polypeptide (the red fluorescent protein) into cells in the pollen grains and into the pollen tubes that germinated from the magnetofected pollen grains.

Example 7

This example illustrates a non-limiting embodiment of a method of providing a genome editing agent to a plant cell, including multiple applications of a magnetic field to a composition including: (a) a plant tissue containing a plant cell; and (b) approximately spherical magnetic nanoparticles of about 150 to about 300 nanometers in diameter that are non-covalently complexed with a genome editing agent; whereby the genome editing agent is delivered to the interior of the plant cell. In this example, a Cas nuclease is delivered to cells in pollen grains, resulting in non-random genomic modification of the cells.

Soybean pollen was collected in the early morning from two commercial soybean varieties (identified here as variety II and variety IW), from both open flowers (anthesis stage) and from closed flowers (with closed corollas, i.e., pre-anthesis stage). Flowers were air-dried for 2 hours before pollen collection. Stamens and anthers were harvested and collected in microfuge tubes, and kept dry prior to the magnetofection process.

A ribonucleoprotein (RNP) including a commercially available Cas nuclease (10 micrograms per millilitre) and a guide RNA (gRNA) targeting the soybean GmSHAT1-5 gene was prepared using a nuclease:gRNA ratio of 6:1 (2 microliters nuclease added to 12 microliters gRNA) and incubated 20 minutes to allow the RNP to form. In some treatment conditions, the RNP-AuMNP preparation included 0.5 microliters of a 10 milligram/millilitre solution of exogenous non-specific DNA (UltraPure™ Salmon Sperm DNA Solution (Invitrogen™), catalogue number 15632011, Thermo Fisher Scientific, Waltham, Mass.) was added to 14 microliters of RNP solution. The RNP was combined with gold magnetic nanoparticles (AuMNPs, 280 nm diameter, purchased from nanoComposix, Inc., San Diego, Calif.) in a 4:1 ratio and incubated at room temperature for 30 minutes.

Just prior to magnetofection, 1 milliliter of soybean germination medium (see Example 1) was added to the microfuge tubes containing the stamens and anthers, and the pollen grains dislodged from the anthers by vortexing. The stamens and anthers were discarded, the dislodged, hydrated pollen grains were collected by centrifugation, and the supernatant discarded. The pollen grains were resuspended in sterile soybean culture medium (15.0 g sucrose per 20 millilitres double-distilled water), divided among replicate sample tubes, and 12.5 microliters of treatment composition (soybean culture medium only for a negative control, AuMNPs without RNP added, the RNP-AuMNP preparation, or the RNP-AuMNP preparation including salmon sperm DNA) added to each sample immediately before magnetofection. The samples were mixed and then set on a magnet. Every 4 minutes, the tubes were shaken to resuspend the pollen and RNP-AuMNP mixture and then placed back on the magnet; this was repeated six times for a total of 7 applications of the magnet (i.e., 7 accelerations of the RNP-AuMNP complexes toward the pollen grains). The pollen grains were then centrifuged and transferred to plates containing solid soybean germination medium for incubation. Seventy-two hours after magnetofection, the pollen grains and emerged pollen tubes were scraped from the solid medium. Liquid soybean germination medium was added to the plates to collect the pollen grains and transferred to microfuge tubes. Pollen grains were centrifuged, the supernatant discarded, and the pollen grains stored at −80 degrees Celsius prior to DNA extraction. Genomic DNA was isolated using Wizard® Magnetic 96 DNA Plant System (catalogue number FF3761, Promega Corporation, Madison, Wis.) and the genomic region encompassing the predicted nuclease cleavage site in the GmSHAT1-5 gene subjected to PCR amplification and sequenced. The results are provided in Table 6. The results indicate a sequence-specific editing efficiency of approximately 2% in pollen grains collected at pre-anthesis stage when exogenous non-specific DNA was included in the editing conditions.

TABLE 6

| Cultivar | Pollen stage | Treatment | % editing |
|---|---|---|---|
| IW | Anthesis | Negative control | 2.84 |
| IW | Anthesis | AuMNP only | 1.95 |
| IW | Anthesis | RNP-AuMNP | 1.89 |
| IW | Anthesis | RNP-AuMNP + DNA | 2.76 |
| IW | Pre-anthesis | Negative control | 2.51 |
| IW | Pre-anthesis | AuMNP only | 2.21 |
| IW | Pre-anthesis | RNP-AuMNP | 1.50 |
| IW | Pre-anthesis | RNP-AuMNP + DNA | 4.54 |
| II | Anthesis | Negative control | 2.54 |
| II | Anthesis | AuMNP only | 1.79 |
| II | Anthesis | RNP-AuMNP | 1.79 |
| II | Anthesis | RNP-AuMNP + DNA | 2.39 |

*percent editing calculated based on the frequency of observed indels

In similar experiments, pollen from maize is collected and magnetofected using multiple accelerations of AuMNPs non-covalently complexed with RNPs toward the pollen grains using procedures similar to those described in this example for soybean pollen. Pollen grains are resuspended in maize pollen germination medium (Example 1) for germination over 3 days. Genomic DNA is extracted from the pollen and the genomic region encompassing the predicted nuclease cleavage site in the target maize gene subjected to PCR amplification and sequenced to verify a non-random genomic modification such as an indel or insertion has occurred at the targeted locus.

All cited patents and patent publications referred to in this application are incorporated herein by reference in their entirety. All of the materials and methods disclosed and claimed herein can be made and used without undue experimentation as instructed by the above disclosure and illustrated by the examples. Although the materials and methods of this disclosure have been described in terms of embodiments and illustrative examples, it will be apparent to those of skill in the art that substitutions and variations can be applied to the materials and methods described herein without departing from the concept, spirit, and scope of the disclosure. For instance, while the particular examples provided illustrate the methods and embodiments described herein using a specific plant, the principles in these examples are applicable to any plant of interest. All such similar substitutes and modifications apparent to those skilled in the art are deemed to be within the spirit, scope, and concept of the disclosure as encompassed by the embodiments recited herein and the specification and appended claims.

What is claimed is:

1. A method of delivering a biological material to the interior of a plant cell, comprising accelerating a biological material/magnetic particle complex multiple times toward a plant cell, wherein the biological material is non-covalently complexed with the magnetic particle, wherein the plant cell is a soybean plant cell that has an intact cell wall, wherein the biological material comprises a material selected from the group consisting of a polynucleotide, a polypeptide, a ribonucleoprotein, a sequence-specific genome editing agent, and a combination thereof and wherein the biological material/magnetic particle complex is accelerated toward the plant cell multiple times by consecutive application of a static magnetic field to the plant cell and biological material/magnetic particle complex followed by separation of the static magnetic field from the plant cell and the biological material/magnetic particle complex, such that the static magnetic field is applied and then discontinued repeatedly, whereby the biological material is delivered to the interior of the plant cell.

2. The method of claim 1, wherein the magnetic particle comprises: (a) a ferromagnetic or superparamagnetic material; (b) an approximately spherical particle of between 150-300 nanometers in diameter; (c) a coating on its surface; or (d) any combination of (a), (b), and (c).

3. The method of claim 1, wherein the magnetic field is (a) non-oscillating or (b) provided by a permanent magnet.

4. The method of claim 1, wherein the soybean plant cell is located in a pre-anthesis-stage pollen grain.

5. The method of claim 1, wherein the soybean plant cell, or a tissue containing the plant cell, or the biological material that is non-covalently complexed with a magnetic particle, is provided in a composition comprising exogenous non-specific DNA.

6. The method of claim 1, wherein the soybean plant cell, or a tissue containing the plant cell, has been pre-treated with an ionic liquid, a surfactant, an enzyme, an abrasive, a solvent, a chelating agent, or a combination thereof.

7. The method of claim 1, wherein the soybean plant cell is a generative cell or a tube cell located in a pollen grain, and wherein the method further comprises germinating the pollen grain.

8. The method of claim 1, wherein the soybean plant cell is a generative cell located in a pollen grain, and wherein the method further comprises germinating the pollen grain and contacting the resulting pollen tube with a stigma, stigma style, ovary, or ovum of a maternal plant, thereby resulting in fertilization of an egg of the maternal plant.

9. The method of claim 8, wherein the biological material comprises a sequence-specific genome editing agent, and wherein a zygote produced by the fertilization comprises a non-random modification in its genome, wherein the non-random genomic modification is effected by the sequence-specific genome editing agent.

10. The method of claim 8, wherein the plant cell is a tube cell located in the pollen grain, and wherein the method further comprises germinating the pollen grain and contacting the resulting pollen tube with a stigma, stigma style, ovary, or ovum of a maternal plant, thereby resulting in fertilization of an egg of the maternal plant.

11. The method of claim 10, wherein the biological material comprises a sequence-specific genome editing agent, and wherein a zygote produced by the fertilization comprises a non-random modification in its genome, wherein the non-random genomic modification is effected by the sequence-specific genome editing agent.

12. A method of providing a genome editing agent to a soybean plant cell, comprising multiple applications of a static magnetic field by consecutive application of the magnetic field followed by withdrawal of the magnetic field to a composition including (a) a plant tissue containing a soybean plant cell, wherein the plant cell has an intact cell wall; and (b) magnetic nanoparticles of about 150 to about 300 nanometers in diameter that are non-covalently complexed with a genome editing agent; whereby the genome editing agent is delivered to the interior of the plant cell.

13. The method of claim 12, wherein the composition comprises a liquid suspension.

14. The method of claim 12, wherein the composition comprises exogenously provided DNA.

15. The method of claim 12, wherein the soybean plant cell is a cell in a plant tissue, a cell in a pollen grain, a cell in a pre-anthesis-stage pollen grain, a cell in a rehydrated pollen grain, a cell of a haploid inducer plant, or a cell in a pollen grain of a haploid inducer plant.

16. The method of claim 12, wherein the genome editing agent is selected from the group consisting of a sequence-specific nuclease, a polynucleotide encoding a sequence-specific nuclease, and a ribonucleoprotein including at least one sequence-specific nuclease.

17. The method of claim 12, resulting in a non-random genomic modification of the plant cell.

18. A plant modification system comprising: (a) a sequence-specific nuclease, or a polynucleotide encoding a sequence-specific nuclease, or a ribonucleoprotein including at least one sequence-specific nuclease non-covalently complexed with an approximately spherical magnetic nanoparticle of about 150 to about 300 nanometers in diameter; (b) a pollen grain comprising a soybean plant cell; (c) a medium containing exogenous non-specific DNA; and (d) a magnet that provides a static magnetic field that is applied and then discontinued repeatedly.

19. The plant modification system of claim 18, wherein the sequence-specific nuclease is a CRISPR Cas nuclease or a CRISPR Cas nuclease ribonucleoprotein including at least one guide RNA.

20. The plant modification system of claim 18, wherein the soybean plant cell is located in a pre-anthesis-stage pollen grain.

21. The plant modification system of claim 18, further comprising at least one component selected from the group consisting of a magnet, a non-oscillating magnetic field, a cell-penetrating peptide, and a nuclear localization signal.

22. The method of claim 1, wherein the consecutive application comprises a first application period of at least five minutes and at least a second application period of at least five minutes.

* * * * *